United States Patent
Buchanan et al.

(10) Patent No.: US 9,545,276 B2
(45) Date of Patent: Jan. 17, 2017

(54) FIXATION DEVICE AND METHOD OF USE FOR A LAPIDUS-TYPE PLANTAR HALLUX VALGUS PROCEDURE

(71) Applicant: Merete Medical GmbH, Berlin (DE)

(72) Inventors: Matthew Buchanan, Falls Church, VA (US); Albert E. Austin, Millersville, MD (US); Emmanuel Anapliotis, Berlin (DE)

(73) Assignee: Aristotech Industries GmbH, Luckenwalde (DE)

( * ) Notice: Subject to any disclaimer, the term of this patent is extended or adjusted under 35 U.S.C. 154(b) by 342 days.

(21) Appl. No.: 14/197,813

(22) Filed: Mar. 5, 2014

(65) Prior Publication Data

US 2014/0277176 A1 Sep. 18, 2014

Related U.S. Application Data

(60) Provisional application No. 61/788,183, filed on Mar. 15, 2013.

(51) Int. Cl.
*A61B 17/80* (2006.01)

(52) U.S. Cl.
CPC ....... *A61B 17/8061* (2013.01); *A61B 17/8014* (2013.01); *A61B 17/8057* (2013.01)

(58) Field of Classification Search
CPC ..... A61B 17/68; A61B 17/80; A61B 17/8004; A61B 17/8014; A61B 17/8023–17/8047; A61B 17/8061; A61B 17/8066–17/8076; A61B 17/8085

(Continued)

(56) References Cited

U.S. PATENT DOCUMENTS

| 2,662,988 A | 12/1935 | McKim |
| 3,741,205 A | 6/1973 | Markolf et al. |

(Continued)

FOREIGN PATENT DOCUMENTS

| AT | 406446 | 5/2000 |
| DE | 3113639 | 5/1982 |

(Continued)

OTHER PUBLICATIONS

International Preliminary Report on Patentability, PCT/IB2014/001111, date of mailing Sep. 24, 2015.

(Continued)

*Primary Examiner* — Todd E Manahan
*Assistant Examiner* — Eric S Gibson
(74) *Attorney, Agent, or Firm* — Andrus Intellectual Property Law, LLP

(57) ABSTRACT

An internal plate fixation device is provided for load bearing and non-load bearing fixation on a plantar side of a metatarsocuneiform joint in a Lapidus procedure. The fixation device includes a U-shaped plate having a plantar section interconnecting a pair of opposed medial legs which are bent relative to the plantar section. The plantar section is formed with a set of threaded fixation holes for receiving locking screws therein. The legs are formed with a set of threaded fixation holes for receiving locking screws therein, and a set of non-threaded fixation holes for receiving temporary K-wires and an interfragmentary compression screw which provides compression and stability at the joint.

1 Claim, 10 Drawing Sheets

(58) Field of Classification Search
USPC .................................................. 606/280–299
See application file for complete search history.

(56) References Cited

U.S. PATENT DOCUMENTS

| | | | |
|---|---|---|---|
| 3,757,591 A | 9/1973 | Taylor | |
| 4,408,601 A | 10/1983 | Wenk | |
| 4,454,876 A | 6/1984 | Mears | |
| 4,573,458 A * | 3/1986 | Lower | A61B 17/8085 606/280 |
| 4,616,634 A | 10/1986 | Vargas Garcia | |
| 4,720,225 A | 1/1988 | Burt | |
| 4,903,691 A | 2/1990 | Heinl | |
| 4,959,065 A | 9/1990 | Arnett et al. | |
| 5,085,660 A * | 2/1992 | Lin | A61B 17/8057 606/288 |
| 5,529,075 A | 6/1996 | Clark | |
| 5,558,674 A * | 9/1996 | Heggeness | A61B 17/1757 606/264 |
| 5,693,055 A * | 12/1997 | Zahiri | A61B 17/8605 606/305 |
| 6,129,728 A | 10/2000 | Schumacher et al. | |
| 6,203,545 B1 | 3/2001 | Stoffella | |
| 6,206,883 B1 | 3/2001 | Tunc | |
| 6,306,140 B1 | 10/2001 | Siddiqui | |
| 6,398,783 B1 | 6/2002 | Michelson | |
| 6,423,068 B1 | 7/2002 | Reisberg et al. | |
| 6,669,701 B2 | 12/2003 | Steiner et al. | |
| 6,716,957 B2 | 4/2004 | Tunc | |
| 6,719,759 B2 | 4/2004 | Wagner et al. | |
| 6,730,091 B1 | 5/2004 | Pfefferle et al. | |
| 6,886,799 B2 | 5/2005 | Yamanashi | |
| 7,008,428 B2 | 3/2006 | Cachia et al. | |
| 7,172,422 B1 * | 2/2007 | Essiger | A61B 17/8038 433/172 |
| 7,354,441 B2 | 4/2008 | Frigg | |
| 7,468,069 B2 * | 12/2008 | Baynham | A61B 17/7059 606/280 |
| 7,655,029 B2 | 2/2010 | Niederberger et al. | |
| 7,771,457 B2 | 8/2010 | Kay et al. | |
| 7,976,570 B2 | 7/2011 | Wagner et al. | |
| 8,118,848 B2 | 2/2012 | Ducharme et al. | |
| 8,246,661 B2 | 8/2012 | Beutter et al. | |
| 8,632,545 B2 | 1/2014 | Sarangapani et al. | |
| 9,271,773 B2 * | 3/2016 | Hwa | A61B 17/809 |
| 2002/0045897 A1 | 4/2002 | Dixon et al. | |
| 2002/0045901 A1 * | 4/2002 | Wagner | A61B 17/8057 606/282 |
| 2002/0183752 A1 | 12/2002 | Steiner et al. | |
| 2003/0060827 A1 * | 3/2003 | Coughln | A61B 17/8061 606/70 |
| 2003/0078668 A1 | 4/2003 | Michelson | |
| 2004/0018228 A1 | 1/2004 | Fischell et al. | |
| 2004/0034356 A1 | 2/2004 | LeHuec et al. | |
| 2004/0073218 A1 | 4/2004 | Dahners | |
| 2004/0097937 A1 * | 5/2004 | Pike | A61B 17/8085 606/282 |
| 2004/0102778 A1 | 5/2004 | Huebner et al. | |
| 2004/0167522 A1 | 8/2004 | Niederberger et al. | |
| 2004/0215192 A1 | 10/2004 | Justis et al. | |
| 2004/0236332 A1 | 11/2004 | Frigg | |
| 2005/0015092 A1 | 1/2005 | Rathbun et al. | |
| 2005/0049594 A1 | 3/2005 | Wack et al. | |
| 2005/0065521 A1 | 3/2005 | Steger et al. | |
| 2005/0085818 A1 | 4/2005 | Huebner | |
| 2005/0090825 A1 * | 4/2005 | Pfefferle | A61B 17/8085 606/283 |
| 2005/0124994 A1 | 6/2005 | Berger et al. | |
| 2005/0165400 A1 | 7/2005 | Fernandez | |
| 2005/0165401 A1 * | 7/2005 | Pack | A61B 17/8863 606/281 |
| 2005/0182408 A1 | 8/2005 | Pfefferle et al. | |
| 2005/0192577 A1 | 9/2005 | Mosca et al. | |
| 2005/0261688 A1 * | 11/2005 | Grady, Jr. | A61B 17/8057 606/286 |
| 2006/0015102 A1 | 1/2006 | Toullec et al. | |
| 2006/0173458 A1 | 8/2006 | Forstein et al. | |
| 2006/0235396 A1 | 10/2006 | Sanders et al. | |
| 2006/0235400 A1 * | 10/2006 | Schneider | A61B 17/8052 606/287 |
| 2006/0241607 A1 | 10/2006 | Myerson et al. | |
| 2007/0016205 A1 * | 1/2007 | Beutter | A61B 17/8057 623/17.11 |
| 2007/0043366 A1 * | 2/2007 | Pfefferle | A61B 17/8052 606/279 |
| 2007/0083207 A1 * | 4/2007 | Ziolo | A61B 17/8057 606/287 |
| 2007/0123885 A1 | 5/2007 | Kirschman | |
| 2007/0233106 A1 | 10/2007 | Horan et al. | |
| 2007/0276386 A1 | 11/2007 | Gerlach et al. | |
| 2008/0015593 A1 * | 1/2008 | Pfefferle | A61B 17/8052 606/282 |
| 2008/0021475 A1 * | 1/2008 | Lawrie | A61B 17/8061 606/319 |
| 2008/0051786 A1 | 2/2008 | Jensen | |
| 2008/0132955 A1 | 6/2008 | Frigg | |
| 2008/0140130 A1 * | 6/2008 | Chan | A61B 17/1728 606/280 |
| 2008/0300637 A1 | 12/2008 | Austin et al. | |
| 2009/0024172 A1 | 1/2009 | Pizzicara | |
| 2009/0171399 A1 * | 7/2009 | White | A61B 17/80 606/286 |
| 2009/0210010 A1 | 8/2009 | Strnad et al. | |
| 2009/0248084 A1 * | 10/2009 | Hintermann | A61B 17/8004 606/286 |
| 2009/0318920 A1 * | 12/2009 | Jacobs | A61B 17/8071 606/70 |
| 2010/0016900 A1 * | 1/2010 | Terres | A61B 17/8019 606/280 |
| 2010/0100134 A1 * | 4/2010 | Mocanu | A61B 17/863 606/281 |
| 2010/0125300 A1 * | 5/2010 | Blitz | A61B 17/8061 606/281 |
| 2010/0131012 A1 * | 5/2010 | Ralph | A61B 17/80 606/280 |
| 2010/0217327 A1 * | 8/2010 | Vancelette | A61B 17/8061 606/281 |
| 2010/0217328 A1 * | 8/2010 | Terrill | A61B 17/8061 606/286 |
| 2010/0256687 A1 * | 10/2010 | Neufeld | A61B 17/80 606/289 |
| 2010/0274293 A1 * | 10/2010 | Terrill | A61B 17/8057 606/286 |
| 2010/0312285 A1 * | 12/2010 | White | A61B 17/8605 606/289 |
| 2010/0312286 A1 * | 12/2010 | Dell'Oca | A61B 17/8057 606/291 |
| 2011/0009866 A1 * | 1/2011 | Johnson | A61B 17/8014 606/70 |
| 2011/0184413 A1 * | 7/2011 | Slater | A61B 17/8061 606/70 |
| 2011/0218626 A1 * | 9/2011 | Krinke | A61B 17/68 623/16.11 |
| 2011/0264148 A1 * | 10/2011 | Prandi | A61B 17/8014 606/286 |
| 2011/0264149 A1 * | 10/2011 | Pappalardo | A61B 17/8019 606/286 |
| 2011/0295324 A1 * | 12/2011 | Donley | A61B 17/8061 606/289 |
| 2011/0295325 A1 | 12/2011 | Wagner et al. | |
| 2012/0065689 A1 * | 3/2012 | Prasad | A61B 17/8085 606/286 |
| 2012/0095465 A1 * | 4/2012 | Graham | A61B 17/809 606/71 |
| 2012/0123484 A1 * | 5/2012 | Lietz | A61B 17/14 606/281 |
| 2012/0143193 A1 * | 6/2012 | Hulliger | A61B 17/8057 606/70 |
| 2012/0165878 A1 * | 6/2012 | Hwa | A61B 17/809 606/280 |

(56) References Cited

U.S. PATENT DOCUMENTS

| | | | |
|---|---|---|---|
| 2012/0209334 A1* | 8/2012 | Lewis | A61B 17/8014 606/286 |
| 2012/0265254 A1 | 10/2012 | Horan et al. | |
| 2012/0303033 A1* | 11/2012 | Weiner | A61B 17/151 606/87 |
| 2013/0023939 A1* | 1/2013 | Pischl | A61B 17/8047 606/286 |
| 2013/0096631 A1* | 4/2013 | Leung | A61B 17/8605 606/286 |
| 2013/0158608 A1* | 6/2013 | Viola | A61B 17/80 606/289 |
| 2013/0165979 A1* | 6/2013 | Greenberg | A61B 17/8061 606/281 |
| 2013/0172942 A1* | 7/2013 | Lewis | A61B 17/8061 606/281 |
| 2013/0190829 A1 | 7/2013 | Batsch et al. | |
| 2013/0211459 A1* | 8/2013 | Horan | A61B 17/8052 606/280 |
| 2013/0338781 A1* | 12/2013 | Bordeaux | A61F 2/30734 623/20.16 |
| 2014/0025123 A1* | 1/2014 | Zeetser | A61B 17/8033 606/289 |
| 2014/0039563 A1* | 2/2014 | Mocanu | A61B 17/8057 606/291 |
| 2014/0066996 A1* | 3/2014 | Price | A61B 17/1728 606/281 |
| 2014/0107798 A1* | 4/2014 | Jeng | A61F 2/4202 623/21.18 |
| 2014/0148859 A1* | 5/2014 | Taylor | A61B 17/8061 606/282 |
| 2014/0172020 A1* | 6/2014 | Gonzalez-Hernandez | A61B 17/80 606/281 |
| 2014/0180343 A1* | 6/2014 | Gaudin | A61B 17/8061 606/283 |
| 2014/0277176 A1* | 9/2014 | Buchanan | A61B 17/8061 606/281 |
| 2015/0142064 A1* | 5/2015 | Perez | A61B 17/8085 606/284 |
| 2015/0223851 A1* | 8/2015 | Hill | A61B 17/8061 606/281 |

FOREIGN PATENT DOCUMENTS

| | | |
|---|---|---|
| DE | 102005044841 | 3/2006 |
| DE | 102006000948 | 10/2006 |
| DE | 102005042766 | 1/2007 |
| DE | 102005043285 | 1/2007 |
| DE | 69835968 | 5/2007 |
| DE | 102009020285 | 11/2010 |
| DE | 102010025001 | 12/2011 |
| EP | 0243114 | 10/1987 |
| EP | 1158916 | 7/2004 |
| EP | 1158915 | 9/2004 |
| EP | 1468655 | 10/2004 |
| EP | 1255498 | 11/2005 |
| EP | 1897509 | 3/2008 |
| EP | 1702577 | 11/2008 |
| EP | 2016918 | 1/2009 |
| EP | 1677693 | 4/2009 |
| FR | 2667913 | 4/1992 |
| FR | 2739151 | 3/1997 |
| FR | 2886535 | 12/2006 |
| WO | 9709000 | 3/1997 |
| WO | 9829058 | 7/1998 |
| WO | 0053110 | 9/2000 |
| WO | 0154601 | 8/2001 |
| WO | 02096309 | 12/2002 |
| WO | 2005041796 | 5/2005 |
| WO | 2005053111 | 6/2005 |
| WO | 2006014436 | 2/2006 |
| WO | 2007025520 | 3/2007 |
| WO | 2010059497 | 5/2010 |
| WO | 2011163092 | 12/2011 |
| WO | 2012000627 | 1/2012 |

OTHER PUBLICATIONS

International Search Report for PCT/DE2012/100248 dated Dec. 20, 2012.

Partial International Search Report for PCT/IB2014/001111 dated Sep. 16, 2014.

International Search Report for PCT/DE2010/075167, mailed Apr. 15, 2011.

Acevedo, Jorge I, Sammarco, V. James, Boucher, Henry R., Parks, Bert G., Schon, Lew C., Myerson, Mark S; Mechanical Comparison of Cyclic Loading in Five Different First Metatarsal Shaft Osteotomies; Foot & Ankle International, Aug. 2002; vol. 23, No. 8, pp. 711-716.

Cisar, J., Holz, U, Jenninger, w., Uhlig. Chr.; Die Osteotomie nach Ludloff bei der Hallux-valgus-Operation; Aktuelle Traumatol. 13; 1983; pp. 247-249.

Hyer, Christopher F., Glover, Jason P., Berlet, Gregory C., Philbin, Terrence, M, Lee, Thomas H.; A Comparison of the Crescentic and Mau Osteotomies for Correction of Hallux Valgus; Journal of Foot and Ankle Surgery; Mar./Apr. 2008; vol. 47, No. 2,; pp. 103-111.

Ludloff, Prof. Dr. K.; Die Beseitigung des Hallux valgus durch die schrage planta-dorsale Osteotomie des Metatarus I.; Arch. Klin. Chir.; 110:364-387; 1918.

Mau, C., Lauber, H.J.; Die operative Behandlung des Hallux valgus (Nachuntersuchungen); 1926, 197:361-377.

Sammarco, V. James; Surgical Strategies: Mau Osteotomy for Correction of Moderate and Severe Hallux Valgus Deformity; Foot & Ankle International; Jul. 2007; 28(7); pp. 857-864.

Saxena, Amol, McCammon, Derek; The Ludloff Osteotomy: A Critical Analysis; Journal of Foot and Ankle Surgery; 1997; vol. 36, No. 2, pp. 100-105.

Trnka, H.-J., Hofstaetter, S.G., Hofstaetter, J.G., Gruber, F., Adams Jr., S.B., Easley, M.E.; Intermediate-Term Results of the Ludloff Osteotomy in One Hundred and Eleven Feet; The Journal of Bone and Joint Surgery; Mar. 2008; vol. 90-A(3); pp. 531-539.

International Search Report for PCT/2006/001508, mailed Feb. 8, 2007.

"Orthopaedic Product News", Aug. 2005, Retrieved from the Internet: URL:http://www.orthoworld.com/us_opn-2005-08.pdf [retrieved on May 26, 2009], p. 30, Hallux Valgus Correction with a Low Profile Locking Plate.

Iselin, Lukas D. et al., Operative Management of Common Forefoot Deformities a Representative Survey of Australian Orthopaedic Surgeons, Foot & Ankle Specialist, vol. X/ No. X, 1-7 (2012).

Miller, Michael J., DMP et al., Inverted Z-scarf Osteotomy for Hallux Valgus Deformity Correction: Intermediate-term Results in 55 Patients, The Journal of Foot and Ankle Surgery, 50: 55-61 (2011).

Dereymaeker, Greta, MD, PhD, Scarf Osteotomy for Correction of Hallux Valgus- Surgical Technique and Results as Compared to Distal Cheveron Osteotomy, The Hallux, vol. 5/ No. 3, 513-523 (Sep. 2000).

Steck, Jerome K., DPM, Long Z-Osteotomy: A Review and New Modification to Correct Troughing, The Journal of Foot and Ankle Surgery, vol. 40/ No. 5, 305-310 (Sep./Oct. 2001).

Adam, Stephanie P., DO et al., Outcomes after Scarf Osteotomy for Treatment of Adult Hallux Valgus Deformity, Clinical Orthopaedics and Related Research, 469: 854-859 (2011).

Trnka, Hans-Jorg, MD et al., Six First Metatarsal Shaft Osteotomies—Mechanical and Immobilization Comparisons, Clinical Orthopaedics and Related Research, No. 381, 256-265 (Mar. 10, 2000).

Aminian, Arash, M.D. et al., Scarf Osteotomy for Hallux Valgus Deformity: An Intermediate Followup of Clinical and Radiographic Outcomes, Foot & Ankle International, vol. 27/ No. 11, 883-886 (Nov. 2006).

(56) References Cited

OTHER PUBLICATIONS

Weil, Lowell Scott, DPM, Scarf Osteotomy for Correction of Hallux Valgus—Historical Perspective, Surgical Technique, and Results, The Hallux, vol. 5/ No. 3, 559-580 (Sep. 2000).

Vienne, Patrick, M.D. et al, Comparative Mechanical Testing of Different Geometric Designs of Distal First Metatarsal Osteotomies, Foot & Ankle International, vol. 28/ No. 2, 232-236 (Feb. 2007).

Lipscombe, Stephen, MRCS et al, Scarf Osteotomy for the Correction of Hallux Valugs: Midterm Clinical Outcome, The Journal of Food and Ankle Surgery, vol. 47/ No. 4, 273-277 ( Jul./Aug. 2008).

Barouk, Louis Samuel, MD, Scarf Osteotomy for Hallux Valgus Correction—Local Anatomy, Surgical Technique, and Combination with Other Forefoot Procedures, The Hallux, vol. 5/ No. 3, 525-557 (Sep. 2000).

Crevoisier, Xavier et al., The Scarf Osteotomy for the Treatment of Hallux Valgus Deformity: A Review of 84 Cases, Foot & Ankle International, vol. 221 No. 12, 970-976 (Dec. 2001).

Coetzee, J. Chris, M.D., Scarf Osteotomy for Hallux Valgus Repair: The Dark Side, Foot & Ankle International, vol. 24/ No. 1, 29-33 (Jan. 2003).

Interventional Procedures Programme—Interventional procedure overview of surgical correction of hallux valgus using minimal access techniques, National Institute for Health and Clinical Excellence, p. 1, 9.

Comparison of Preoperative to Postoperative Measurement at 6 Weeks, 1 and 2 Years Postoperative, Table 1.

O'Briain, David E. et al., Use of a Geometric Formula to Improve the Radiographic Correction Achieved by the Scarf Osteotomy, Foot & Ankle International, vol. 33/ No. 8, 647-654 (Aug. 2012).

Easley, Mark E., M.D., et al., Current Concepts Review: Hallux Valgus Part II: Operative Treatment, Foot & Ankle International, vol. 28/ No. 6, 748-758 (Jun. 2007).

International Search Report and Written Opinion for PCT/IB2014/001111, dated Sep. 8, 2014.

Myerson, Mark, M.D., "Correction of Hallux Valgus Deformity with the Ludloff Osteotomy Surgical Technique", Joint Meeting of American Orthopedic Foot & Ankle Society and the Japanese Surgery Society for the Foot, Nov. 13-15, 1997, Waikoloa, HI.

\* cited by examiner

FIXATION DEVICE AND METHOD OF USE FOR A LAPIDUS-TYPE PLANTAR HALLUX VALGUS PROCEDURE

CROSS-REFERENCE TO RELATED APPLICATION

The present application relates to and claims the benefit and priority of U.S. Provisional Patent Application No. 61/788,183 filed Mar. 15, 2013, which is fully incorporated herein by reference.

FIELD

The present disclosure relates generally to foot and ankle surgery, and more particularly, pertains to a fixation device used in a Lapidus-type procedure for surgically correcting a hallux valgus deformity in the first metatarsocuneiform joint of the foot.

SUMMARY

The present inventors have recognized that the prior art does not disclose any internal fixation plate or method of use that is particularly useful in the Lapidus procedure, provides a combined medial, plantar and interfragmentary fixation specific to the Lapidus hallux valgus procedure, and permits non-load bearing or load bearing post-operative care of a person having undergone Lapidus-type surgical repair of the hallux valgus.

The present inventors have sought to provide an internal fixation plate that allows for surgical correction, internal placement of the internal fixation plate, completion and internal fixation of the internal fixation plate and final internal fixation of the internal fixation plate following the Lapidus procedure to repair the hallux valgus.

In one example disclosed herein, an internal fixation device is provided for use in fixation of a metatarsocuneiform joint. The fixation device includes a fixation plate contoured relative to intersecting x, y and z axes extending perpendicular to each other. The fixation plate has a U-shape when viewed in an xy plane defined by the x and y axes and includes an upper surface, a lower surface and a plantar section having opposite proximal and distal ends extending along the x axis with the y axis extending transversely to and bisecting the plantar section. The plantar section interconnects a pair of opposed medial legs which are bent relative to the plantar section, and extend from the opposite proximal and distal ends of the plantar section with respect to the x and y axes. The plantar section is formed therethrough with a set of threaded fixation holes. Each of the legs is formed therethrough with a set of threaded and non-threaded fixation holes spaced further away from the y axis than the threaded fixation holes in the plantar section.

Preferably, the plantar section includes a pair of spaced apart threaded fixation screw holes which are formed angularly through a thickness of the plantar section. The threaded fixation holes in the plantar section are located at opposite ends thereof. A first arcuate guide wall is provided on the upper surface of the fixation plate of the plantar section, and extends partially around a top of one of the threaded fixation holes. A second arcuate guide wall is provided on the lower surface of the fixation plate of the plantar section, and extends partially around a bottom of one of the threaded fixation holes. The upper surface of the fixation plate of the plantar section is provided with a first grooved channel defining a bending area located between the threaded fixation holes. Each leg has a single threaded fixation hole which is located adjacent an outer end of each leg. In a top view of the fixation plate, the legs are bent rearwardly of the plantar section. One of the legs has a length which is longer than a length of the other leg. The plantar section has a thickness which is greater than a thickness of the legs to allow bending of the legs beyond an initial bent curvature thereof. One of the legs is formed with a slotted non-threaded temporary fixation hole. The upper surface of the fixation plate of the one of the legs is formed with a second grooved channel defining a bending area located between the one of the legs and the slotted temporary fixation hole. One of the legs includes a non-threaded interfragmentary screw hole which is formed angularly through a thickness of the one of the legs. A first arcuate guide wall is provided on the upper surface of the fixation plate of the one of the legs, and extends partially around a top of the interfragmentary screw hole. The upper surface of the fixation plate of the one of the legs is formed with a concave recess leading into the interfragmentary screw hole. A second arcuate guide wall is provided on the lower surface of the fixation plate of the one of the legs, and extends partially around a bottom of the interfragmentary screw hole. The lower surface of the fixation plate of the one of the legs is formed with a concave recess leading from the interfragmentary screw hole. The upper surface of the fixation plate of the one of the legs is provided with third and fourth grooved channels defining bending areas on opposite sides of the interfragmentary screw hole. The one of the legs is formed therethrough with a non-threaded circular temporary fixation hole. The threaded fixation screw holes are formed with axes that extend dorsal and slightly distal relative to the plantar section. The threaded fixation holes provided in the legs are formed with axes that extend substantially perpendicularly to the upper surface and the lower surface of the fixation plate. The interfragmentary screw hole is formed with an axis that extends proximal and slightly dorsal in a direction relative to one of the legs. The fixation plate is configured to be engaged on a cuneiform and a first metatarsal bone during and after a Lapidus procedure. The fixation plate has a continuous outer edge that forms an outer extent of all of the U-shape when viewed in the xy plane.

In another example, an internal fixation device used in fixation of a metatarsocuneiform joint defined between a cuneiform and a metatarsal bone includes a U-shaped plate having an upper surface and a lower surface. The U-shaped plate further has a plantar section transferring to and interconnecting a pair of opposed proximal and distal medial legs which are bent relative to the plantar section. The plantar section is formed therethrough with a proximal threaded fixation screw hole and a distal threaded fixation screw hole, and each leg is formed therethrough with a threaded fixation screw hole at a distal end of each leg. The legs are each formed with a non-threaded fixation hole. A proximal locking bone fastener is received in the proximal threaded fixation screw hole of the plantar section. A distal locking bone fastener is received in the distal threaded fixation screw hole of the plantar section. A proximal locking bone fastener is received in the threaded fixation screw hole of the proximal leg. A distal locking bone fastener is received in the threaded fixation screw hole of the distal leg. A non-locking interfragmentary compression bone fastener is received in the non-threaded fixation hole of the distal leg.

Each bone fastener is typically a cannulated screw adapted to receive a K-wire. The non-locking bone fastener includes a shaft which is partially threaded along a lower portion thereof. The locking bone fasteners have shafts which are threaded along entire lengths thereof. The proximal and distal locking bone fasteners are received in the plantar section such that outer ends of the plantar section locking bone fasteners point in a dorsal and slightly distal direction relative to the plantar section, and are configured for engagement with the cuneiform and the metatarsal bone. The proximal and distal locking bone fasteners are received in the leg such that outer ends of the leg locking bone fasteners point in a lateral direction relative to the legs, and are configured for engagement with the cuneiform and the metatarsal bone. The non-locking interfragmentary compression screw is received in the distal leg such that an outer end of the interfragmentary screw points in a proximal and slightly distal direction relative to the distal leg, and is configured for engagement with the cuneiform and the metatarsal bone across the metatarsocuneiform joint.

In another example, a surgical method of fixating a metatarsocuneiform joint between a cuneiform and a metatarsal bone in a Lapidus procedure to correct a hallux valgus deformity includes the steps of: a) providing a U-shaped plate configured to be engaged on a cuneiform and metatarsal bone, the plate having a plantar section interconnecting a pair of proximal and distal opposed legs which are bent relative to the plantar section, wherein the plantar section is formed therethrough with a proximal threaded fixation hole and a distal threaded fixation hole, and wherein each of the proximal and distal legs is formed with a threaded fixation hole and a non-threaded fixation hole and the distal leg is further formed with a non-threaded fixation hole; b) entering the tissues of a foot affected with a hallux valgus deformity using a longitudinally medial incision to gain exposure to a metatarsocuneiform joint; c) positioning the plate across a plantar side of the exposed metatarsocuneiform joint such that outer ends of the legs extend upwardly from the plantar section; d) temporarily fixing the plate across the metatarsocuneiform joint by inserting a K-wire in the non-threaded fixation holes of the legs; e) inserting a non-locking interfragmentary compression screw through the non-threaded fixation hole in the distal leg into the metatarsal bone and a cuneiform across the metatarsocuneiform joint; f) inserting proximal and distal threaded locking screws through the threaded fixation holes in the plantar section into the cuneiform and the metatarsal bone to secure the plantar section across the metatarsocuneiform joint; and g) inserting proximal and distal threaded locking screws through the threaded fixation holes in the legs into the cuneiform and the metatarsal bone to secure the legs on opposite sides of the metatarsocuneiform joint and complete fixation of the plate.

BRIEF DESCRIPTION OF THE DRAWINGS

The drawings illustrate the best mode presently contemplated under 35 U.S.C. §112.

DETAILED DESCRIPTION

Figure 1:
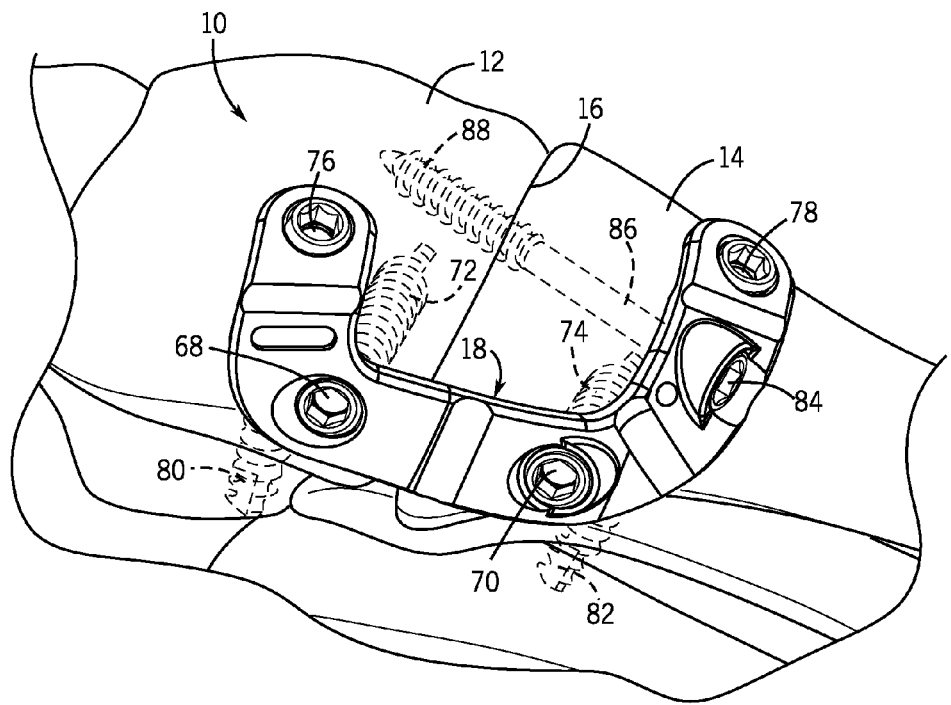
FIG. 1 is a perspective view of an exemplary internal fixation device mounted at a metatarsocuneiform joint of a foot following a Lapidus procedure to correct a hallux valgus deformity.

For purposes of promoting an understanding of the principles of the invention, reference will now be made to the examples illustrated in the drawings and described in the following written specification. It is understood that no limitation to the scope of the invention is thereby intended. It is further understood that the present invention includes any alterations and modifications to the illustrated example and includes further applications of the principles of the invention as would normally occur to one skilled in the art to which this invention pertains.

Prior Hallux Valgus Correction and Fixation

A hallux valgus deformity of the forefoot is characterized by lateral deviation (i.e. away from the centerline of the body) of the hallux formed by the proximal phalanx and the distal phalanx, and medial deviation (i.e. towards the center of the body, hallux varus) of the first metatarsal bone or metatarsus. This condition can lead to painful motion of the first metatarsophalangeal (MTP) joint, and adjustments in gait that may ultimately cause problems further up the leg.

Historically, many different surgical procedures have been proposed to correct hallux valgus deformities. In the majority of cases, the surgical treatment involves a osteotomy to correct structural deformities associated with the first metatarsal bone and the hallux phalanges, relieve symptoms and pain and restore proper foot function. The osteotomy results in the creation and correction of metatarsal segments used to return the metatarsus and MTP joint to their normal anatomical positions and restore acceptable hallux valgus. In any osteotomy, it is essential that a fixation device, such as screws, K-wires, pins, plates and the like, be used to maintain correction of the metatarsal segments until bone union occurs.

One well-known surgical operation used for correcting hallux valgus deformities is the Lapidus-type procedure. As first introduced in 1934, the Lapidus procedure involves completing an arthrodesis or fusion of the first metatarsocuneiform joint in the foot in order to attain a desired hallux valgus correction. The metatarsocuneiform joint consists of the first metatarsal long bone of the foot and the first cuneiform bone of the foot which is located just proximal or behind the first metatarsal bone. An arthrodesis or fusion consists of connecting bones together to relieve pain associated with the two bones of the metatarsocuneiform joint rubbing together and causing pain. Arthrodesis, also known as artificial ankylosis or syndesis, is the artificial induction of joint ossification between two bones via surgery. This is done to relieve intractable pain in a joint which cannot be managed by pain medication, splints or other normally indicated treatments. The typical causes of such pain are fractures which disrupt the joint and arthritis. It is mostly commonly preferred on joints in the spine, hand, ankle and foot. Since its introduction, the Lapidus procedure has gained popularity throughout the world for hallux valgus correction.

A Lapidus surgical procedure entails making a dorsal or medial skin incision which begins just proximal to the metatarsocuneiform joint of the foot extending to the base of the first metatarsal bone. Once exposure is obtained, the surgeon prepares the joint of the metatarsocuneiform for fusion or arthrodesis. Preparation entails removing any articular cartilage that may remain on the two joint surfaces, and the object is to expose healthy, bleeding cancellous bone on both sides of the joint in order to obtain an arthrodesis of the joint. Exposing healthy, bleeding cancellous bone is important to allow the two bones to be fused together creating the arthrodesis. A number of variations to the Lapidus procedure has occurred over the years, and reported in the literature which allows a surgeon to prepare the joint surface for a fusion. The object of the Lapidus procedure is to realign the two joint surfaces between the first metatarsal bone and the first cuneiform bone in order to achieve correction of the hallux valgus deformity. Various methods of temporary correction are utilized whether manually, or with the use of instruments or guides to temporarily achieve the appropriate correction position of the metatarsocuneiform joint to achieve correction of the hallux valgus deformity.

Once the Lapidus procedure has been performed and the metatarsocuneiform joint is positioned properly to achieve correction of the hallux valgus deformity, the metatarsocuneiform joint has been previously fixated with various types of screws, metal K-wires, dorsal plates, medial plates, and offset medial plates, but most notably with either screws or medial plates. The fixation techniques reported vary in steps, screw diameter size used, K-wires used, placement, plates, etc.

Historically, the Lapidus procedure has encountered various reported issues with achieving the object of fusing or obtaining an arthrodesis of the metatarsocuneiform joint. There are reported problems with non-unions occurring and requirements for the patient to be non-weight bearing for significant periods in order to achieve the union or arthrodesis of the metatarsocuneiform joint. A non-union occurs when the two bones of the metatarsocuneiform joint fail to fuse together after the Lapidus procedure.

The Present Fixation Device and Method of Use

Referring now to the drawings, the present disclosure describes an internal plate fixation device 10 and method of use for obtaining a more rigid, stable and precise fixation of the hallux valgus correction in a Lapidus procedure than previously known.

FIG. 1 illustrates a portion of a left forefoot including a first or medial cuneiform 12, and a first metatarsal bone 14 which together define a first metatarsocuneiform joint 16 therebetween. The fixation device 10 is shown fixed to the cuneiform 12 and the metatarsal bone 14, and positioned across a plantar (tension) side of the metatarsocuneiform joint 16 following a Lapidus procedure to correct the hallux valgus deformity.

Figure 2:
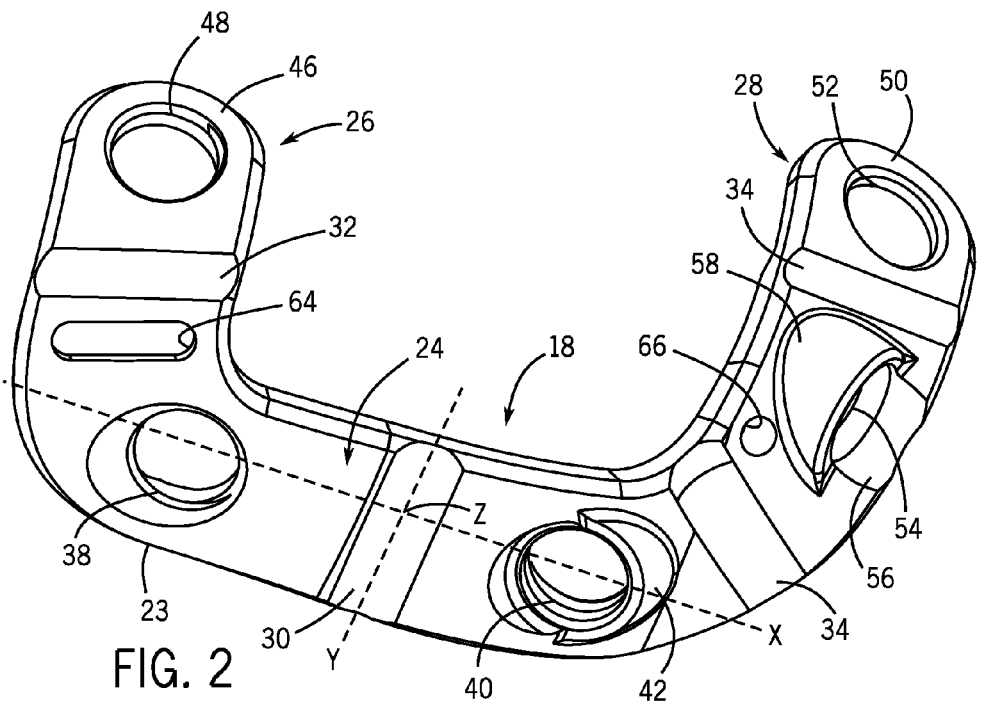
FIG. 2 is a perspective view of a fixation plate of the fixation device shown in FIG. 1.
Figure 7:
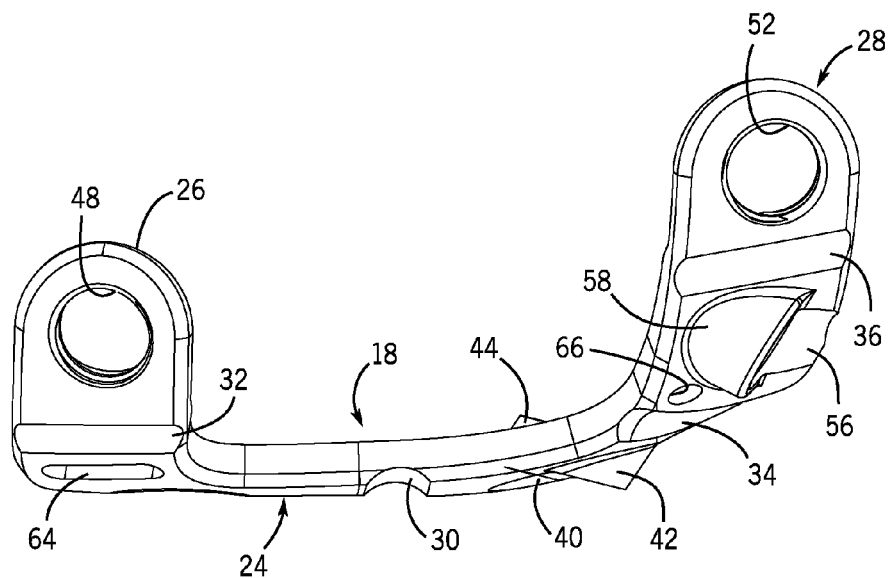
FIG. 7 is a view of the fixation plate shown in FIG. 3 rotated forwardly.
Figure 8:
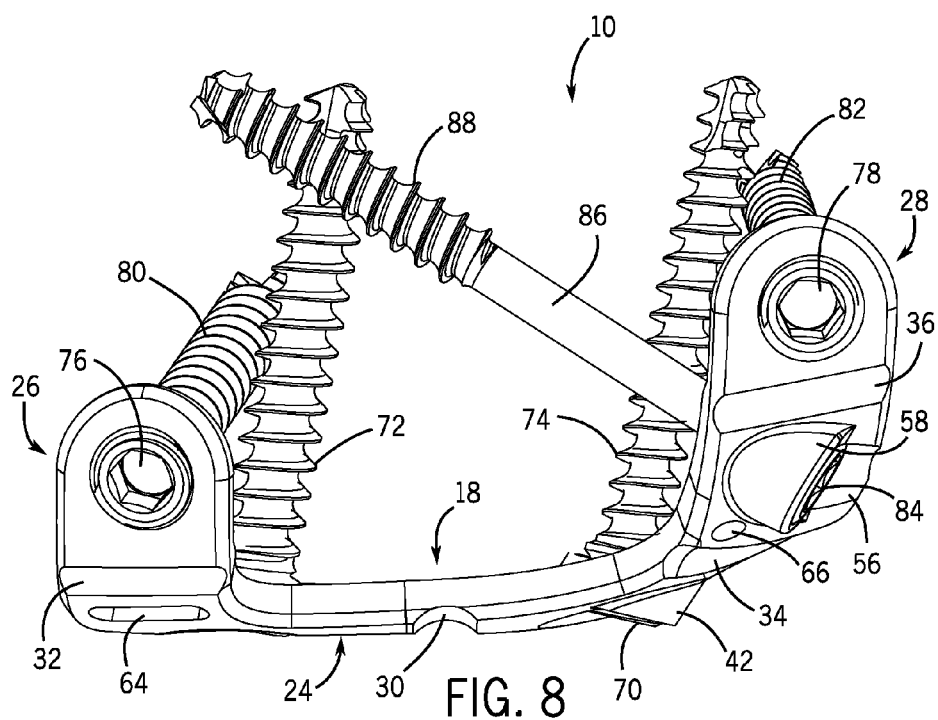
FIG. 8 is a view similar to FIG. 7 showing the fixation plate with various fixation screws.
Figure 9:
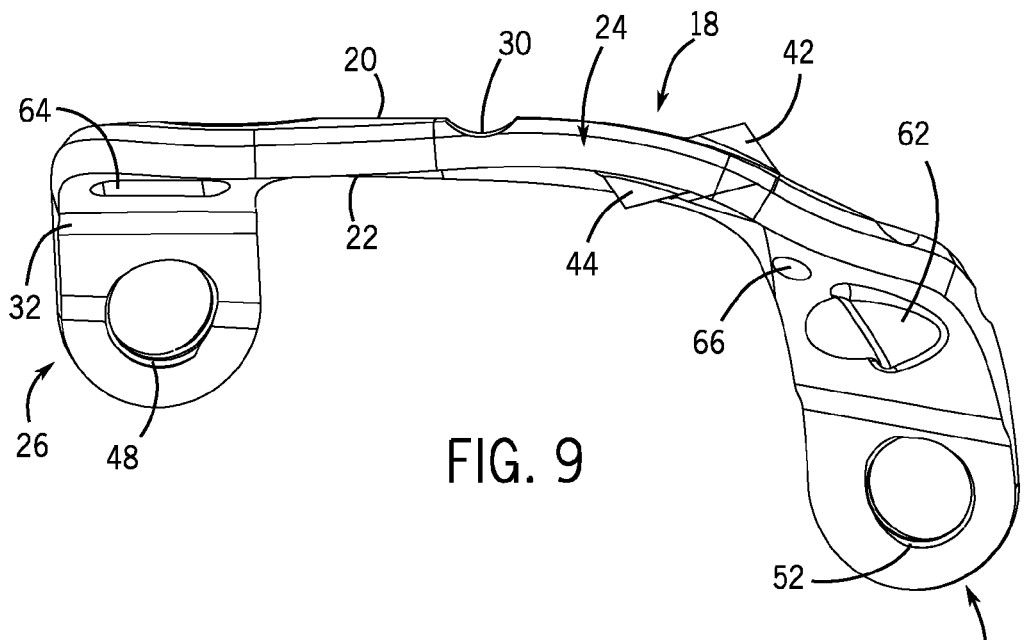
FIG. 9 is a view of the fixation plate shown in FIG. 3 rotated rearwardly.
Figure 10:
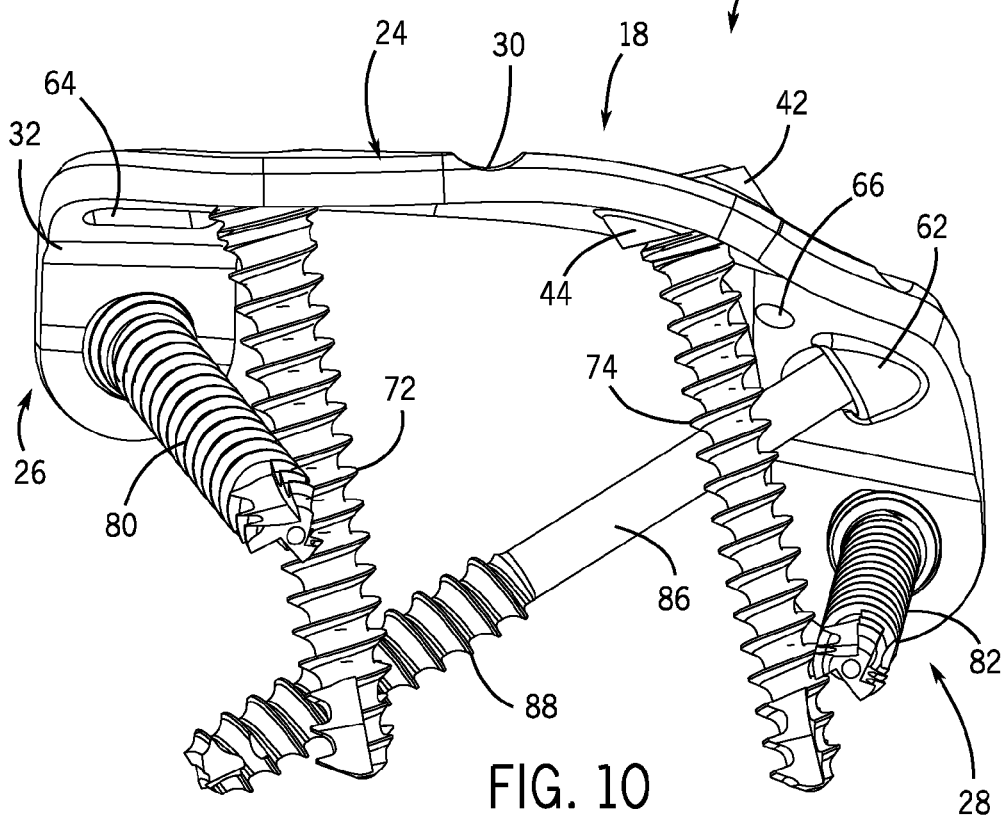
FIG. 10 is a view similar to FIG. 9 showing the fixation plate with various fixation screws.
Figure 11:
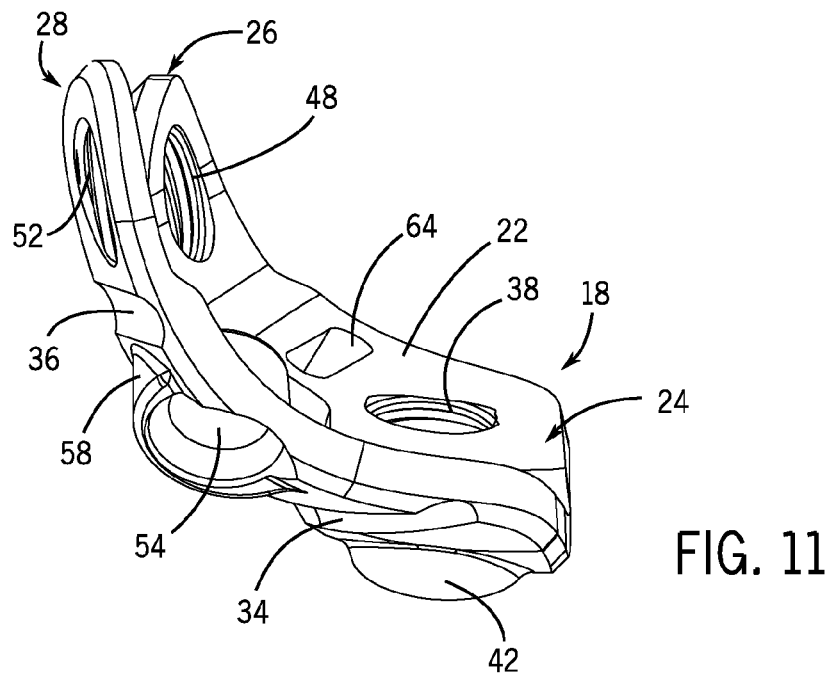
FIG. 11 is a view of the fixation plate taken from the right-hand side of FIG. 3.
Figure 12:
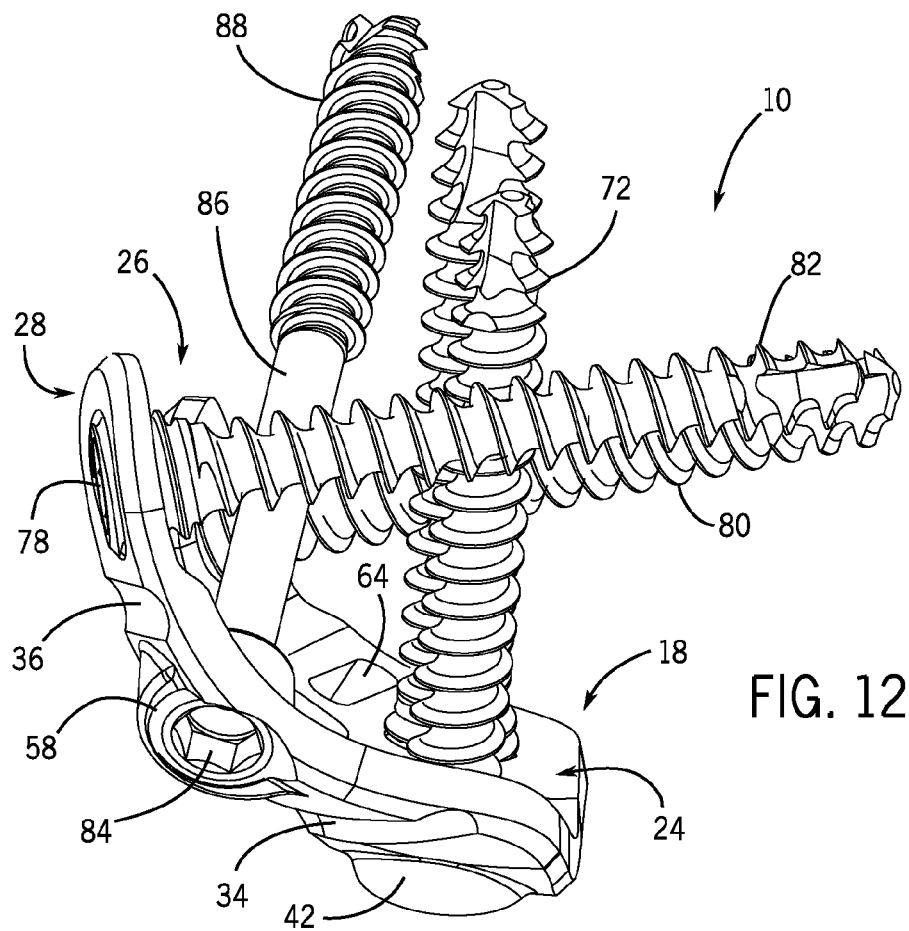
FIG. 12 is a view similar to FIG. 11 showing the fixation plate with various fixation screws.

Referring to FIGS. 2-12, the fixation device 10 includes a unitary medial and plantar internal fixation plate 18 contoured relative to longitudinally extending x, laterally extending y and vertically extending z axes laying perpendicularly to each other as shown in FIG. 2. The fixation plate 18 has an upper surface 20 and a lower bone-contacting surface 22 configured with a curvature for mounting on outer curved surfaces of the cuneiform 12 and the metatarsal bone 14. The plate 18 has a U-shape when viewed in an xy plane defined by the xy axes. The fixation plate has a continuous outer edge 23 that forms an outer extent of the entire U-shape when viewed in the xy plane. The plate 18 has a plantar section 24 having opposite sides extending in the direction of the x axis with the y axis extending transversely relative thereto, and bisecting the plantar section 24. The plantar section 24 transfers to and interconnects a single pair of opposed medial sections in the form of proximal and distal legs 26, 28, respectively, which are bent rearwardly of the plantar section 24 on only one side thereof and in a direction of the y and z axes into an initial curvature. The legs 26, 28 extend away from each other on opposite sides of the plantar section 24. The distal leg 28 is formed with a length that is slightly longer than the length of the proximal leg 26. The plantar section 24 is configured to engage both the cuneiform 12 and the metatarsal bone 14, and extend across the metatarsocuneiform joint 16. The medial sections or legs 26, 28 are anatomically contoured such that the leg 26 engages the cuneiform 12, and the leg 28 engages the metatarsal bone 14. As seen in FIGS. 7 and 9, the plantar section 24 is formed with a slight twist as it transitions toward the leg 28.

The fixation plate 18 can be constructed of titanium, titanium alloy, stainless steel, plastic, resorbable material, any metal alloy or other suitable material, and is preferably made from titanium alloy. In the exemplary embodiment, the fixation plate 18 is configured with a varied thickness in the plantar section 24 and the medial sections or legs 26, 28 as represented, for example, in FIGS. 2 and 7. Thickness of the fixation plate 18 is greater in the plantar section 24 across the plantar side of the metatarsocuneiform joint 16 to provide strength across the joint site.

Figure 3:
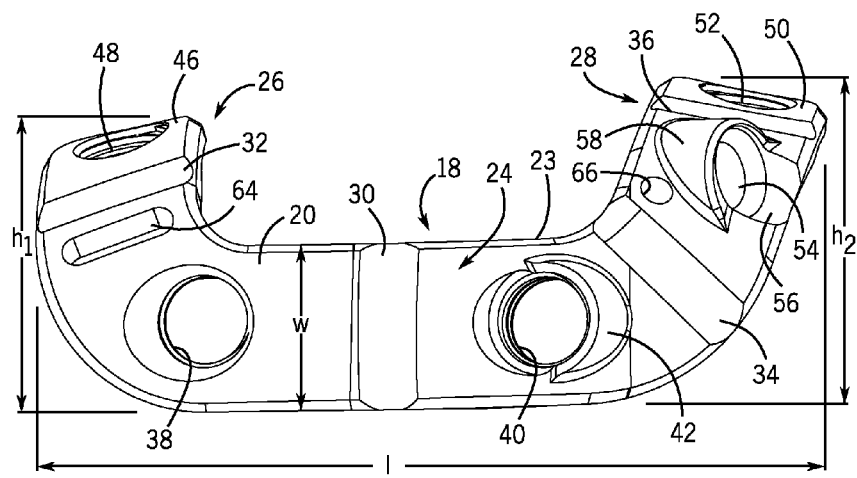
FIG. 3 is a top plan view of the fixation plate shown in FIG. 2.

Thickness of the fixation plate 18 is thinner across the respective proximal and distal medial sections or legs 26, 28 to enable low profile fixation of the plate 18 to the cuneiform 12 and the metatarsal bone 14, and to allow bending of the plate 18, if desired, when used in the surgical procedure. Typically, the plantar section 24 has a thickness of no more than 1.8 millimeters and the legs 26, 28 have a thickness of no more than 1.0 millimeter. Although not limited to these dimensions, the fixation plate 18, as shown in FIG. 3, typically has a length l of about 36.3 millimeters, a width w of about 8.0 millimeters, a height $h_1$ of proximal leg 26 of about 18 millimeters and a height $h_2$ of distal leg 28 of about 23 millimeters.

In the exemplary embodiment, the upper surface 20 of the fixation plate 18 is formed across the width thereof with a number of grooved channels defining bending areas for providing additional flexibility in assisting the surgeon with bending of the fixation plate 18. More specifically, a first grooved channel 30 is provided in the plantar section 24, a second grooved channel 32 is provided in the leg 26 and respective third and fourth grooved channels 34, 36 are provided in the distal leg 28.

Figure 5:
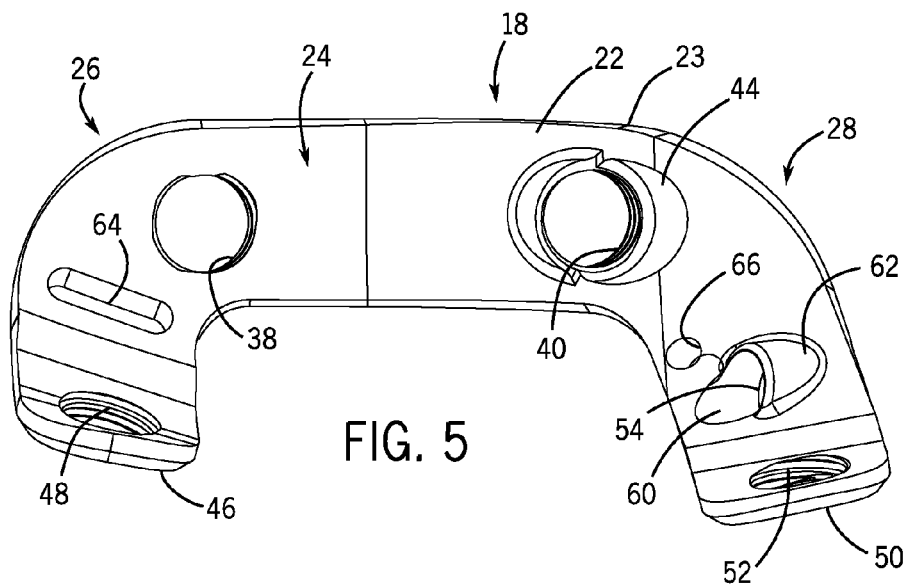
FIG. 5 is a bottom view of the fixation plate shown in FIG. 3.
Figure 6:
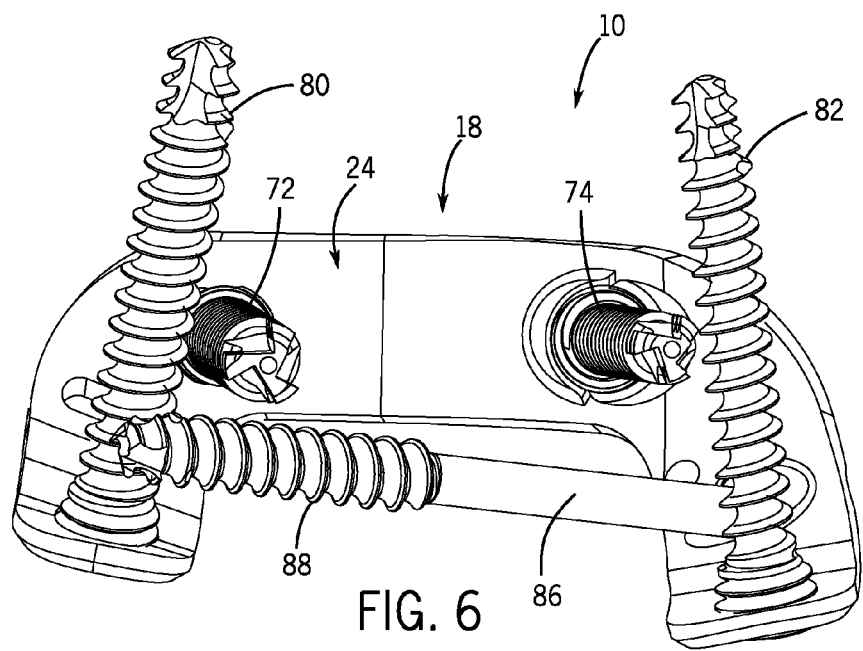
FIG. 6 is a view similar to FIG. 5 showing the fixation plate provided with various fixation screws.

The fixation plate 18 includes a plurality of set of fixation holes that extend completely through the thickness of the plate 18. Such fixation holes are non-locking (i.e. non-threaded) or locking (i.e. threaded) for receiving K-wires or bone fasteners in the form of cannulated (hollow) screws which are known to slide over the K-wires. More particularly, opposite ends of the plantar section 24 are provided on opposite sides of the first grooved channel 30 with a proximal threaded plantar screw hole 38 and a distal threaded plantar screw hole 40. Both of the threaded plantar screw holes 38, 40 are formed angularly through the plantar section 24 along axes which are dorsal and slightly distal in direction relative to the plantar section 24. An arcuate guide wall 42 rises at an angle from the upper surface 20, and extends partially around the top of the screw hole 40 such as seen in FIGS. 2 and 3. An arcuate guide wall 44 projects at an angle from the lower surface 22, and extends partially around the bottom of screw hole 40 such as depicted in FIG. 5. Diameters of the plantar screw holes 38, 40 are substantially equal.

The proximal medial section or leg 26 is formed at an outer end 46 thereof with a threaded medial screw hole 48. The distal medial section or leg 28 is likewise formed at an outer end 50 thereof with a threaded medial screw hole 52. Axes of the threaded medial screw holes 48, 52 extend generally perpendicularly to the upper surface 20 and the lower surface 22. Diameters of the screw holes 48, 52 are substantially equal. The threaded screw holes 38, 40, 48, 52 define fixation holes which are used in the fixation of the fixation plate 18 to the cuneiform 12 and the metatarsal bone 14. The threaded screw holes 48, 52 are located outside of the threaded screw holes 38, 40, and beyond the opposite proximal and distal ends of the plantar section 24 such that the threaded holes 48, 52 are spaced further away than the threaded holes 38, 40 from the y axis.

In addition, the distal medial section or leg 28 is provided with a non-threaded interfragmentary screw hole 54 which is located between the third grooved channel 34 and the fourth grooved channel 36. The interfragmentary screw hole 54 is formed angularly through a generally central section of the distal leg 28 along an axis which is proximal and slightly dorsal in direction relative to the leg 28. A portion of the upper surface 20 is formed with a concave recess 56 leading from the outer peripheral edge 23 into the interfragmentary screw hole 54. An arcuate guide wall 58 projects at an angle from the upper surface 20, and extends partially around the top of the interfragmentary screw hole 54. A portion of the lower surface 22 is formed with a concave recess 60 exiting from the interfragmentary screw hole 54. An arcuate guide wall 62 extends angularly from the lower surface 22 around a portion of the interfragmentary screw hole 54 at the bottom thereof. The interfragmentary screw hole 54 defines a fixation hole used in fixing the fixation plate 18 across the metatarsocuneiform joint 16.

The fixation plate 18 further includes temporary fixation holes for temporarily fixing the plate 18 to the cuneiform 12 or the metatarsal bone 14 before a final fixation of the plate 18. One temporary fixation hole, as shown in FIGS. 2 and 3, is located in the proximal leg 26 between the second grooved channel 32 and the plantar screw hole 38, and is formed as an elongated slot 64 extending through the thickness of the fixation plate 18. Another temporary fixation hole is formed as a small circular hole 66 positioned on the distal leg 28 between the third grooved channel 34 and the arcuate guide wall 58. The circular hole 66 extends through the thickness of the fixation plate 18, and has a diameter which is smaller than any of the screw holes 38, 40, 48, 52, 54.

Referring to FIGS. 4, 6, 8, 10 and 12, a proximal plantar locking screw 68 is received in the threaded plantar screw hole 38. A distal plantar locking screw 70 is received in the threaded plantar screw hole 40. A locking screw as used herein is defined as any screw that is locked by threads to the fixation plate 18. The locking screws 68, 70 have respective shafts 72, 74 which are variously threaded along substantially entire lengths thereof, and extend at an angle relative to the plantar section 24. The plantar locking screws 68, 70 when locked in the fixation plate 18 are designed to have outer ends of the shafts 72, 74 that point in a dorsal slightly distal direction, as seen in phantom lines of FIG. 1. The plantar locking screws 68, 70 typically have a diameter of 3.5 millimeters and a length of 12-32 millimeters.

Figure 4:
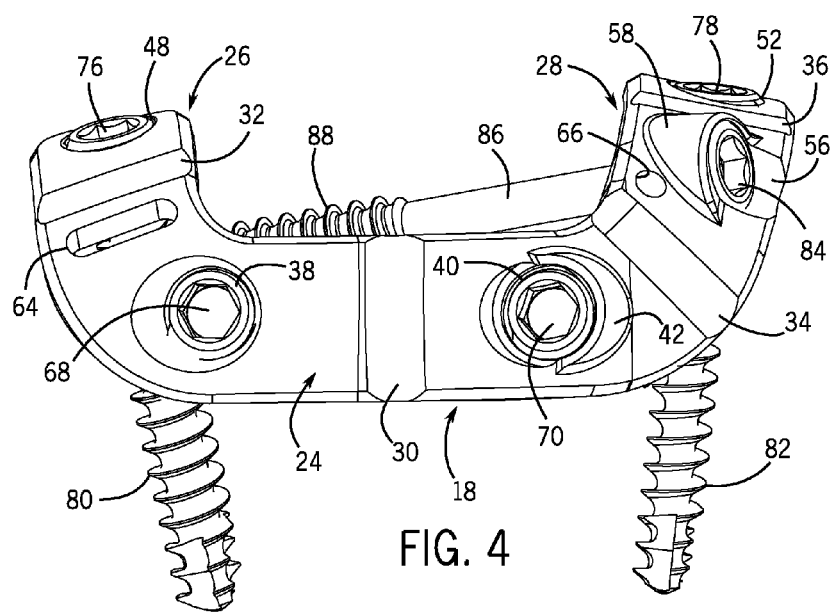
FIG. 4 is a view similar to FIG. 3 showing the fixation plate provided with various fixation screws.

A proximal medial locking screw 76 is received in the threaded medial locking screw hole 48, and a distal medial locking screw 78 is received in the threaded medial locking screw hole 52. The medial locking screws 76, 78 have respective shafts 80, 82 which are variously threaded along substantially entire lengths thereof. The medial locking screws 76, 78 when locked in the fixation plate 18 are designed to have outer ends of the shafts 80, 82 that extend in a lateral direction as depicted in FIG. 4. The medial locking screws 76, 78 typically have a diameter of 3.0 millimeters and a length of 12-32 millimeters. The locking screws 68, 70, 76, 78 are provided to enable final fixation of the plate 18 to the cuneiform 12 and the metatarsal bone 14 as will be further described below.

A non-locking interfragmentary compression screw 84 is received in the non-threaded interfragmentary screw hole 54, and is designed to cross the metatarsocuneiform joint 16 following the Lapidus procedure. The interfragmentary compression screw 84 is also designed to provide compression between fractured fragments at the joint 16, and to enhance stability and promote healing for an arthrodesis procedure. A non-locking screw as used herein, is defined as any screw that is not locked to the plate 18 by threads. The screw 84 has a shaft 86 which is partially threaded at 88 along a lower portion thereof. The screw 84 is guided at an angle relative to the leg 28 by the concave recess 56, the arcuate guide wall 58, the concave recess 60 and the arcuate guide wall 62 so that an outer end of the shaft 86 extends in a proximal and slightly distal direction as seen in phantom lines in FIG. 1. The interfragmentary compression screw 84 typically is a cannulated screw having a diameter of 3.0 millimeters and a length of 12-40 millimeters.

It should be understood that the plate 18 can be constructed to accommodate variously sized diameter locking or non-locking screws with other than those diameter sizes described herein that thread and lock in the plate 18, or that fixate to the plate 18, but do not lock and thread in the plate 18. It should likewise be appreciated that the plate 18 can be variously sized to accommodate a variety of cuneiform and first metatarsal bone anatomies.

The fixation device 10 is particularly useful in connection with a Lapidus procedure for correcting a hallux valgus deformity at a surgically altered metatarsocuneiform joint 16. The goal of the Lapidus procedure is to correct and stabilize the first metatarsal bone 14 at the apex of the hallux valgus deformity. The fixation plate 18 is designed to be advantageously positioned on the tension (plantar) side of the metatarsocuneiform joint 16, The Lapidus procedure commences with a longitudinal medial incision centered slightly plantar to midline over the medial aspect of the first tarsal-metatarsal or metatarsocuneiform joint (MTCJ) 16. Such incision allows for placement of the fixation device 10 as well as excellent exposure of the MTCJ 16. This incision may be extended distally to the first metatarsophalangeal joint (MTP) to enable resection of the medial eminence. A second incision may be indicated to allow for release of the anterior adductor tendon.

Next, the deep fascia covering the anterior tibial tendon is identified, and a longitudinal incision is made to expose the tendon and the capsule of the MTCJ 16. The plate 18 is designed to lay on the plantar surface of the broad insertion of this tendon. The MTCJ 16 is exposed through a longitudinal capsular incision made dorsal to the anterior tibial tendon. The MTCJ 16 is opened and preparation of the joint surface proceeds with the goal to expose healthy, cancellous bone on both sides of the MTCJ 16. The first metatarsal bone 14 is then adducted and plantarflexed as needed to obtain an acceptable position. A number of known intraoperative techniques may be used to obtain proper preparation for positioning of the plate 18.

Figure 13:
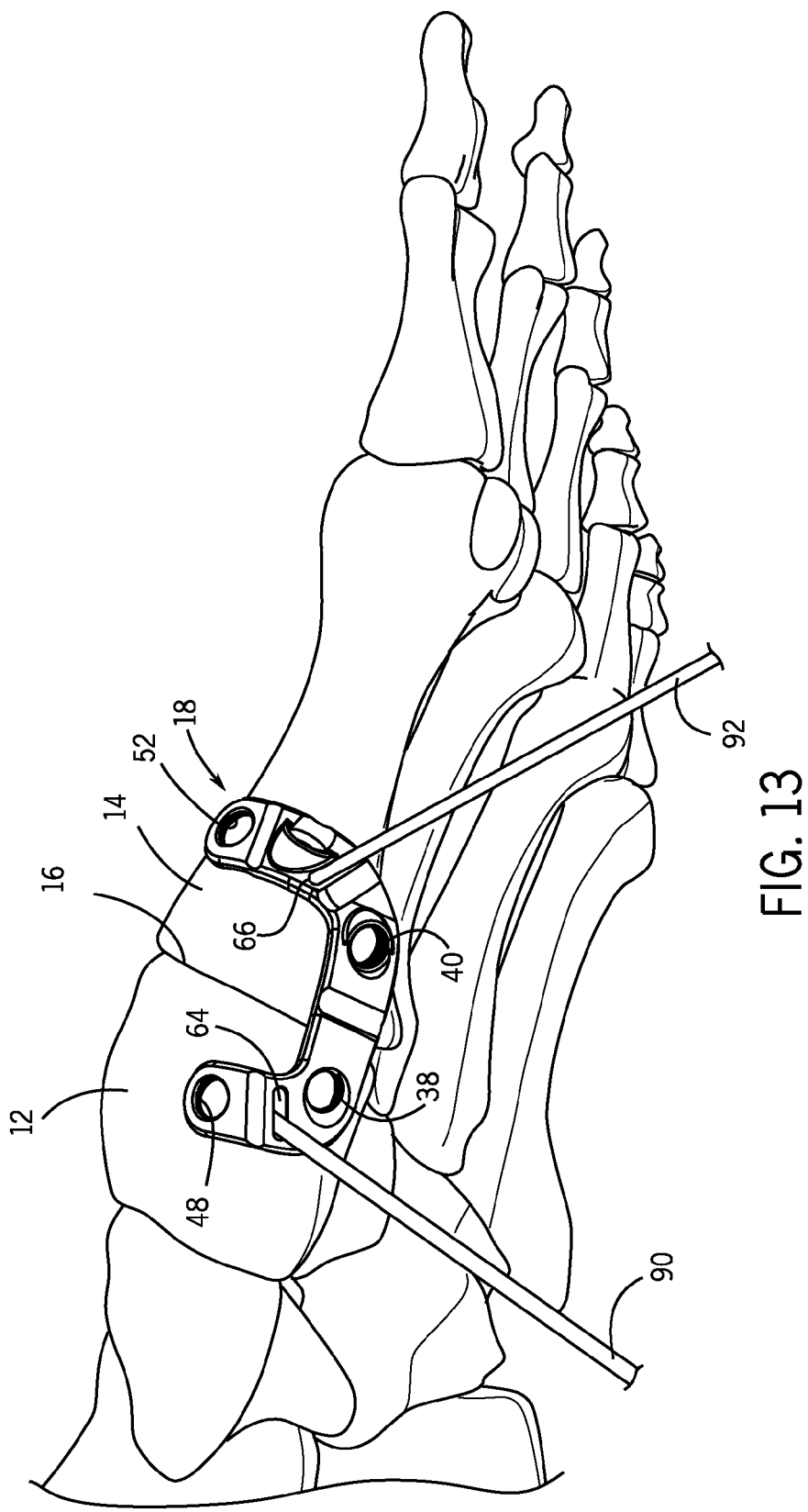
FIG. 13 is a perspective view of the initial positioning and temporary fixing of the fixation plate on the metatarsocuneiform joint at the beginning of a Lapidus procedure.

Referring to FIG. 13, once the MTCJ 16 has been exposed and prepared, the fixation plate 18 is manually positioned along the plantar surface and across the MTCJ 16. As shown, the plantar section 24 spans the MTCJ 16 and the outer ends 46, 50 of the legs 26, 28, respectively extend upwardly from the plantar section 24 with the threaded holes 38, 48 overlying the cuneiform 12. The threaded holes 40, 52 as well as the non-threaded hole 54 overlie the metatarsal bone 14. The plate 18 is anatomically designed to match the contour of the plantar surface of the MTCJ 16 and does not routinely require bending. If necessary, however, the plate 18 may be bent as desired using bending instruments and ensuring a contoured fit. Bending is assisted by the provision of the grooved channels 30, 32, 34, 36 and the decreased thickness of the legs 26, 28 relative to the plantar section 24. Once proper placement of the plate 18 over the MTCJ 16 is achieved, a K-wire 90 is inserted through the non-threaded slotted hole 64 located on the cuneiform side of the MTCJ 16 to temporarily fix the plate 18. The K-wire 90 is preferably placed in the most proximal end portion of the hole 64 to allow for compression of the MTCJ 16 when positioning the interfragmentary compression screw 84. An additional K-wire 92 can also be inserted through the non-threaded circular hole 66 overlying the metatarsal bone 14 to temporarily fix the plate 18.

Figure 14:
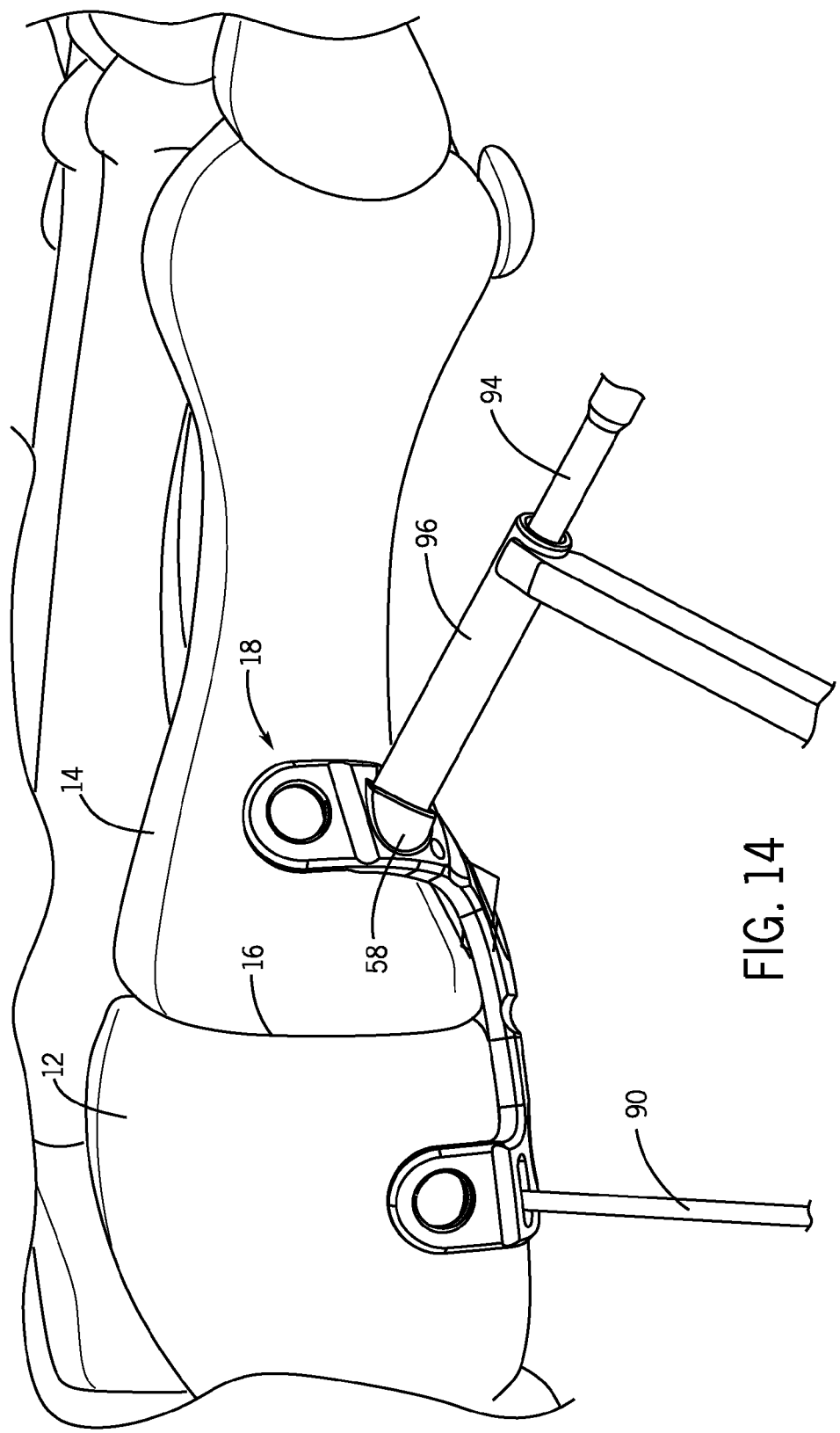
FIG. 14 is a perspective view of the fixation plate showing a drill guide inserted through a hole in the fixation plate for receiving an interfragmentary compression screw used in the fixation of the device.

Next, a K-wire 94 is inserted through a drill guide 96 inserted into the interfragmentary screw hole 54 as directed by the guide wall 58 such as depicted in FIG. 14. The K-wire 94 is typically used with depth gauge to measure an appropriate depth for the interfragmentary compression screw 84. A drill bit is inserted over the K-wire 94 and within the drill guide 96, and an appropriate hole is drilled across the MTCJ 16 through the metatarsal bone 14 and the cuneiform 12. With the drill guide 96 removed, the cannulated interfragmentary compression screw 84 is inserted over the K-wire 94, and the screw 84 is tightened through the hole formed across the MTCJ 16 to compress the MTCJ 16. Fluoroscan imaging is used to confirm proper placement of plate 18 and anatomic osseous alignment.

Figure 15:
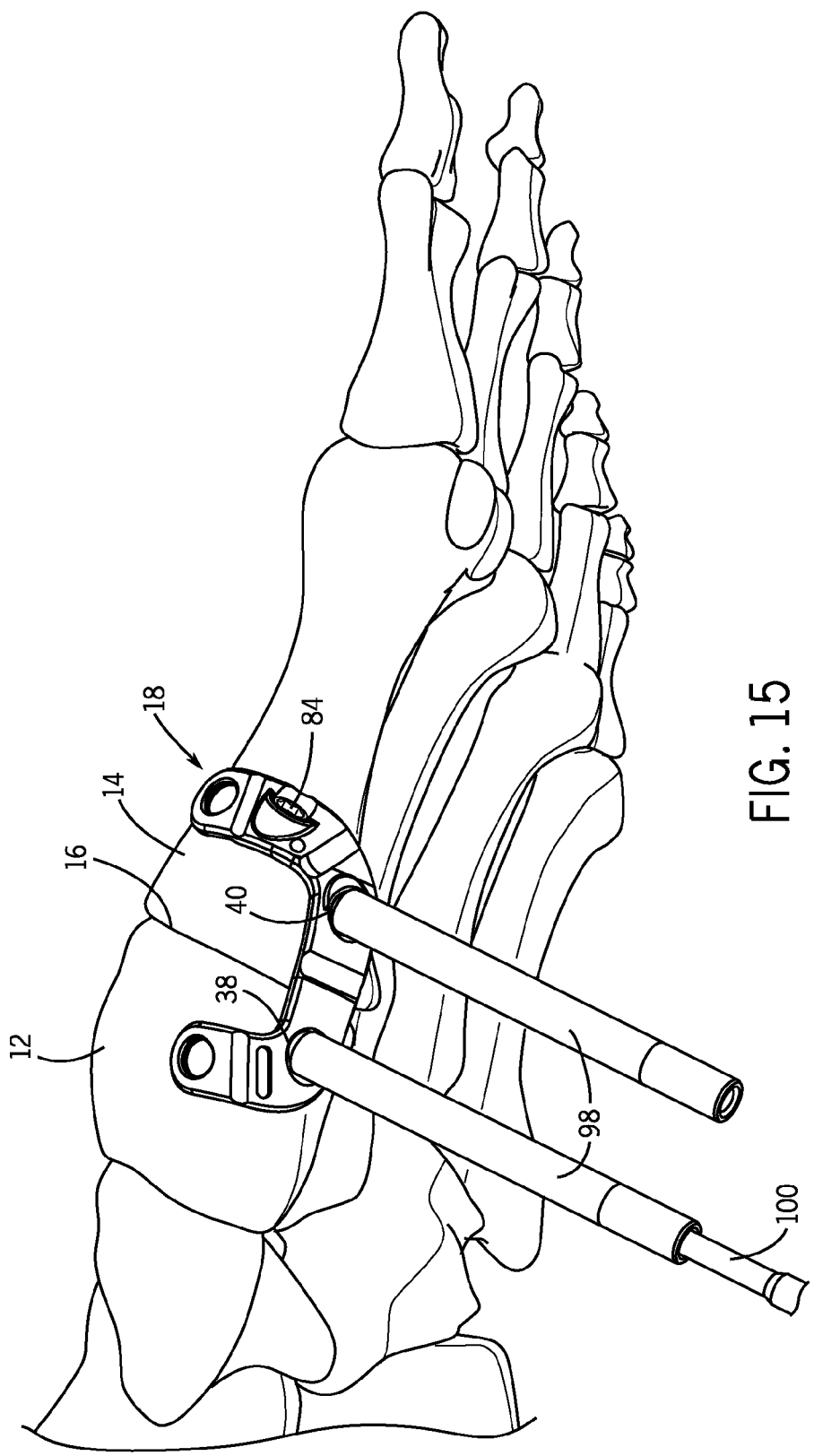
FIG. 15 is a perspective view of the fixation plate showing drill guides inserted through holes in the fixation plate for receiving plantar locking screws.

Referring to FIG. 15, once the interfragmentary compression screw 84 has been inserted across the MTCJ 16, K-wire 92 is removed and threaded drill guides 98 are placed within the plantar threaded holes 38, 40 of the plate 18. A K-wire, such as shown at 100, is inserted in each drill guide 98 and used with a depth gauge to measure appropriate depths for the plantar screws 68, 70. A drill bit is inserted over each K-wire 100 within each drill guide 98 and appropriate holes are drilled in the cuneiform 12 and the metatarsal bone 14. The drill guides 98 are removed and the plantar screws 68, 70 are inserted over the K-wires 100 and screwed into the formed holes to fixate the plantar section 24 to the cuneiform 12 and the metatarsal bone 14.

Figure 16:
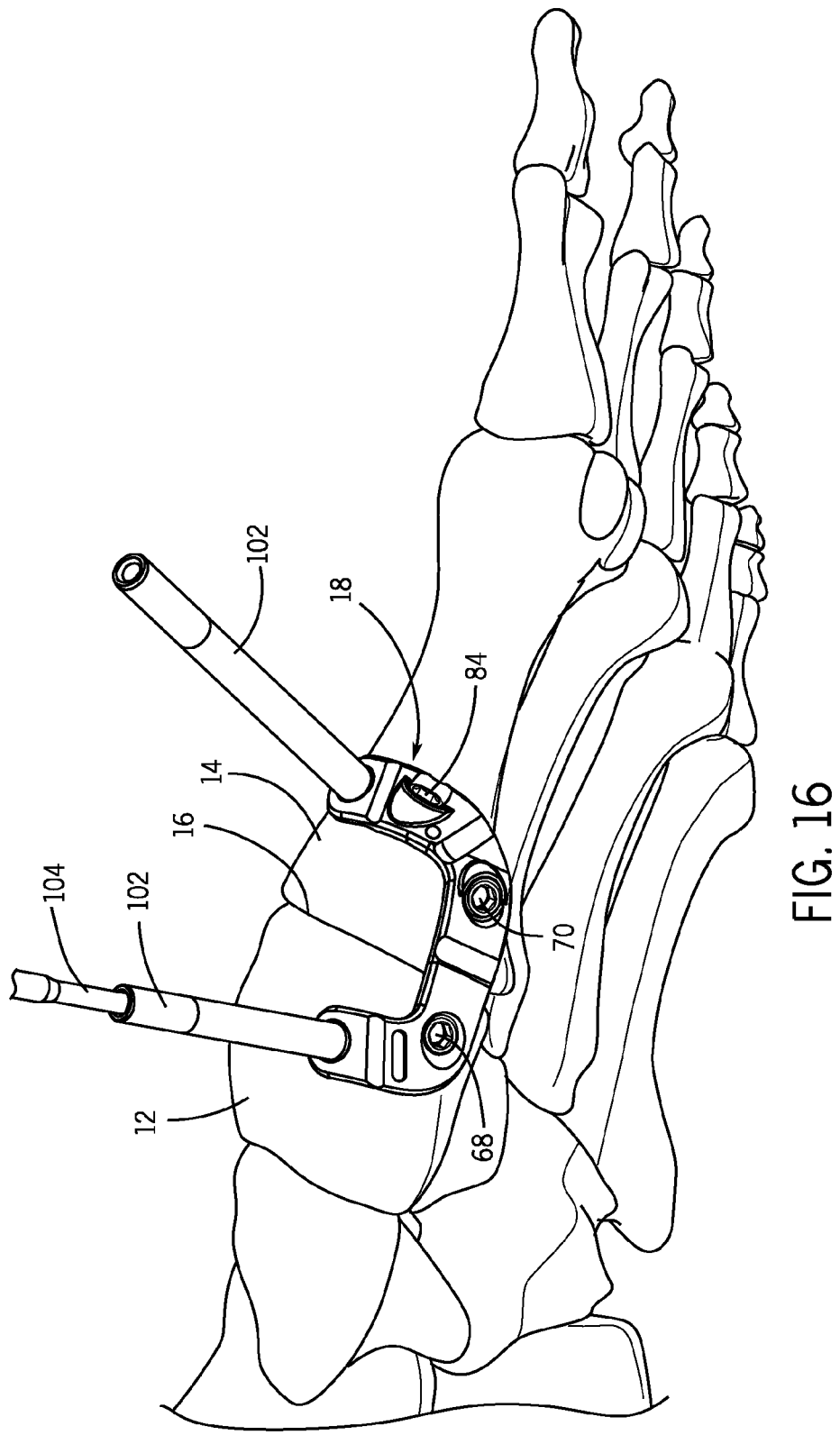
FIG. 16 is a perspective view of the fixation plate having drill guides inserted through holes in the fixation plate for receiving medial locking screws.

As depicted in FIG. 16, once the plantar screws 68, 70 have been inserted, drill guides 102 are threaded into the threaded leg holes 48, 52 and used with K-wires, such as shown at 104, to measure the appropriate depth for the medial screws 76, 78. Holes are appropriately drilled, and the medial screws 76, 78 are screwed into the formed holes to finally fixate the plate 18 across the MTCJ 16 to the cuneiform 12 and the metatarsal bone 14. Wounds at the site are closed in standard fashion by the surgeon.

If desired or necessary, the legs 26, 28 may be further bent to adjust to the particular contour of the joint site before final fixation. This is made possible by the bending areas defined by the grooved channels 30, 32, 34, 36 and the decreased thickness of the legs 26, 28 as compared to the plantar section 24.

It is contemplated that the internal fixation plate 18 described herein can be provided in a kit or case with plates 18 of multiple sizes for the left and right forefoot with multiple locking and non-locking bone fasteners or screws 68, 70, 76, 78, 84 and with various tools, instruments, guides and the like to give a surgeon flexibility in selecting the desired means for securing the plate 18 across the MTCJ 16.

The fixation device 10 shown and described provides an internal plantar and medial fixation plate that allows for surgical correction of a hallux valgus deformity, precise placement of the fixation plate, placement of an interfragmentary screw fixation and final fixation of the metatarsal cuneiform joint 16 to complete the Lapidus procedure. The fixation device 10 provides for both non-load and load bearing union at the metatarsocuneiform joint 16. Advantageously, the fixation plate 18 can withstand the weight-bearing capacity of the normal human being and the weight-bearing load displaced to the joint 16 when undergoing the normal walking gait cycle, thus making it an option to bear weight immediately following fixation of the plate 18 after the Lapidus procedure eliminating the concern of non-unions. The fixation device 10 provides the interfragmentary compression screw 84 across the joint 16 to enhance stability and promote healing for the arthrodesis procedure.

In addition, the fixation device 10 is precisely fixed on the plantar (tension) side of the metatarsocuneiform joint 16 to provide a biomechanically superior construct for fusion. The locking screws 68, 70, 76, 78 are positioned to achieve rigid stabilization transferring the weight bearing to the plate 18 and not the surgical site. The plate 18 is formed slightly thicker across the plantar section 24 than the legs 26, 28 to provide strength across the joint 16.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims, if they have structural elements that do not differ from the literal language of the claims, or if they include equivalent structural elements with insubstantial differences from the literal language of the claims.

Various alternatives and embodiments are contemplated as being within the scope of the following claims, particularly pointing out and distinctly claiming the subject matter regarded as the invention.

What is claimed is:

1. A Lapidus plantar fixation device configured for fixation of a metatarsocuneiform joint between a cuneiform and a metatarsal bone during a Lapidus procedure, the fixation device comprising:
  a fixation plate contoured relative to intersecting x, y and z axes extending perpendicular to each other;
  the fixation plate having a U-shape when viewed in an xy plane defined by the x and y axes and including an upper surface, a lower surface and a plantar section having opposite proximal and distal ends extending along the x axis with the y axis extending transversely to and bisecting the plantar section, the plantar section interconnecting a pair of opposed medial legs which are bent relative to the plantar section and extend from the opposite proximal and distal ends of the plantar section with respect to the x and z axes;
  wherein the plantar section is formed therethrough with a pair of threaded fixation holes located at opposite ends thereof and formed angularly therethrough a thickness of the plantar section;
  wherein each of the legs is formed therethrough with threaded and non-threaded fixation holes spaced further away from the y axis than the threaded fixation holes in the plantar section;
  wherein, in the xy plane, the legs are bent rearwardly of the plantar section and the fixation plate has a continuous outer edge that forms an outer extent of all the U-shape when viewed in the xy plane;
  wherein each leg has a single threaded fixation hole located adjacent an outer end of each leg, and one of the legs has a length which is longer than a length of the other leg;
  wherein a first arcuate guide wall projects angularly from the upper surface of the fixation plate of the plantar section, and extends partially around a top of one of the threaded fixation holes in the plantar section, and a second arcuate guide wall projects angularly from the lower surface of the fixation plate of the plantar section, and extends partially around a bottom of the one of the threaded fixation holes in the plantar section;
  wherein the upper surface of the fixation plate of the plantar section is formed with a first grooved channel defining a first bending area located between the threaded fixation holes of the plantar section and extending along the y axis across an entire width of the plantar section;
  wherein the other of the legs is formed therethrough with a slotted non-threaded temporary fixation hole located between the first grooved channel and the threaded fixation hole on the other of the legs;
  wherein the upper surface of the fixation plate of the other of the legs is formed with a second grooved channel defining a bending area located between the threaded fixation hole on the other of the legs and the slotted temporary fixation hole, and extending across an entire width of the other of the legs;
  wherein the one of the legs includes an interfragmentary screw hole which is formed angularly through a thickness of the one of the legs;
  wherein a first arcuate guide wall projects angularly from the upper surface of the fixation plate on the one of the legs, and extends partially around a top of the interfragmentary screw hole;
  wherein the upper surface of the fixation plate of the one of the legs is formed with a concave recess leading from the outer edge of the fixation plate into the interfragmentary screw hole;
  wherein a second arcuate guide wall projects angularly from the lower surface of the fixation plate of the one of the legs, and extends partially around a bottom of the interfragmentary screw hole;
  wherein the lower surface of the fixation plate of the one of the legs is formed with a concave recess;
  wherein the upper surface of the fixation plate of the one of the legs is provided with third and fourth grooved channels defining bending areas on opposite sides of the interfragmentary screw hole and extending across an entire width of the one of the legs;
  wherein the one of the legs is formed therethrough with a non-threaded circular temporary fixation hole between the third and fourth grooved channels;
  wherein the plantar section is adapted to engage the cuneiform and the metatarsal bone and extend across the metatarsocuneiform joint;
  wherein the other of the legs is adapted to engage the cuneiform and the one of the legs is configured to engage the metatarsal bone;
  wherein the plantar section is configured with a twist as the plantar section transitions toward the one of the legs; and
  wherein the interfragmentary screw hole defines an axis that extends proximal and slightly dorsal in a direction relative to the one of the legs, the axis being adapted to pass through the metatarsal cuneiform joint and configured to cross axes formed through the threaded screw holes in the plantar section.

* * * * *